United States Patent [19]

Chernin

[11] 4,209,232

[45] Jun. 24, 1980

[54] MULTIPLE REFLECTION OPTICAL SYSTEM

[76] Inventor: Semen M. Chernin, prospekt Vernadskogo, 58, kv. 49, Moscow, U.S.S.R.

[21] Appl. No.: 15,218

[22] Filed: Feb. 26, 1979

[51] Int. Cl.² .............................................. G02B 5/10
[52] U.S. Cl. ..................................... 350/294; 356/246
[58] Field of Search ........................ 350/294; 356/246

[56] References Cited

U.S. PATENT DOCUMENTS 3,469,920   9/1969   Dumartin et al. .................... 356/246

OTHER PUBLICATIONS

Smith, H. D. et al., *J.O.S.A.*, vol. 30, Aug. 1940, pp. 338-342.

White, John U., *J.O.S.A.*, vol. 32, May 1942, pp. 285-288.

*Primary Examiner*—Jon W. Henry
*Attorney, Agent, or Firm*—Lackenbach, Lilling & Siegel

[57] ABSTRACT

The multiple reflection optical system includes opposing reflecting members of which one is adjoined by entrance and exit slits and is made up of two identical mirrors defining a group arranged symmetrically with respect to one of the slits. The other reflecting member is made up of two concave mirrors of different dimensions. The spacing between the group of the identical mirrors and the concave mirrors, as well as the focal length of the concave mirror of the smaller dimensions are 1.5 times the focal length of the concave mirror of the greater dimensions.

1 Claim, 3 Drawing Figures

MULTIPLE REFLECTION OPTICAL SYSTEM

The invention relates to the art of making optical instrumentation, and, more particularly, it relates to multiple reflection optical systems.

FIELD OF INVENTION

The present invention can be used to utmost effectiveness in infrared spectrophotometry. Furthermore, the invention can be utilized in optical gas analyzers for high-speed analysis of complex gas mixtures and blends, e.g. for quantitative determination of atmospheric pollution, which has been gaining importance as part of the environment control methods.

BACKGROUND OF INVENTION

At present, in order to step up the response at absorpion measurements in spectrophotometry, there is practiced repeated passage of radiation through an absorbing layer. To attain this, there are used various combinations of mirrors that transfer a light flux from a source through the absorbing medium with minimum losses. The range of practical applications of multiple reflection mirror systems is vast, including as it does both unique high-temperature units for investigating the spectra of hard-volatile compounds and serially produced spectral instruments. At present, the complete set of every infrared spectrophotometer includes a cell with an extended optical path for investigating either gases contained in extra-small concentrations, or else those of which the absorption band is very weak. Absorption cells of this kind are employed in both qualitative and quantitative analysis.

There is known a multipassage optical system (see, for instance, Journal of the Opt. Soc. of Am., 1940, Vol. 30, p. 338) comprising a mirror objective with the focal length F at one side, and two field mirrors arranged at an angle to each other—at the opposite side, and also the entrance and exit slits adjoining these mirrors. Flat mirrors are employed as field ones, with the mirror lens being positioned at the double focal length from the field mirrors.

In the aforedescribed system, as the intermediate images of the entrance slit are focused on the planar surfaces, no compression of the outermost beams takes place, whereby the multiple reflection results in a significant portion of the radiation being scattered beyond the edges of the mirror lens—the so-called inclined beam vignetting phenomenon.

There is further known a multiple reflection optical system (see, for instance, Journal of the Opt. Soc. of Am., 1942, Vol. 32, p. 285) comprising opposing reflecting members of which one is adjoined by the entrance and exit slits, and others are made up of two concave mirrors. The reflecting member adjoined by the entrance and exit slits is likewise shaped as a concave mirror, all the mirrors having the same focal length, and the spacing of the opposing mirrors being twice the focal length.

The last-described optical system of the prior art forms a system of related images on the reflecting surfaces of the mirrors. With beams making a four-run passage in the system, the first (in the beam direction) concave mirror transmits the image of the entrance slit illuminated by the source onto the surface of the opposing concave mirror. The latter forms the image of the first concave mirror on the other concave mirror, adjoining it, the last-mentioned concave mirror being used to transfer the intermediate image of the entrance slit from the aforesaid opposing concave mirror to the exit slit of the system.

By varying the angle between the concave mirrors opposing the entrance and exit slits, the sytem is tunable for a multiple (in excess of four-run) passage of the beams. However, but a slight maladjustment of the system renders the latter inoperative.

With the optical system of the prior art including similar concave mirrors arranged in opposition to the slits, the relative aperture of the system directly related to the geometric dimensions of the first concave mirror in the beam direction has proved to be inadequate for conducting an essential number of investigations in the infrared region of the operation.

It is an object of the present invention to increase the relative aperture of the system.

This object is attained in a multiple reflection optical system comprising opposing reflecting members of which one is adjoined by the entrance slit and the exit slit and otheis are made up of two concave mirrors in which system, in accordance with the present invention, the concave mirrors have different geometric dimensions, the reflecting member adjoining the slits being made up of two identical mirrors defining a group arranged symmetrically relative to one of the slits, the spacing between the group of the identical mirrors and the concave mirrors, as well as the focal length of the smaller concave mirror being about 1.5 times the focal length of the greater concave mirror.

In the disclosed optical system the relative aperture has been stepped up and the aberrations have been reduced. The disclosed system, furthermore, offers an optical path length which is 1.5 times that of cells with the fixed passage of the radiation and of given dimensions suited to fit the standard types of spectrophotometer. The rational arrangement of the mirrors enables the use of standard cylindrical tubes for the manufacture of the cells, instead of chambers of sophisticated configurations, which is particularly essential when the gas cells are rated for operation under gauge pressure. The disclosed optical system enables the light beams to be utilized to the fullest degree over the entire diameter of the cell, and is useful as an all-purpose multi-passage cell in all kinds of infrared spectrophotometers.

BRIEF DESCRIPTION OF DRAWINGS

The essence of the invention will be further described in connection with the embodiment thereof, with reference being had to the appended drawings wherein.

Figures 1, 2, 3:
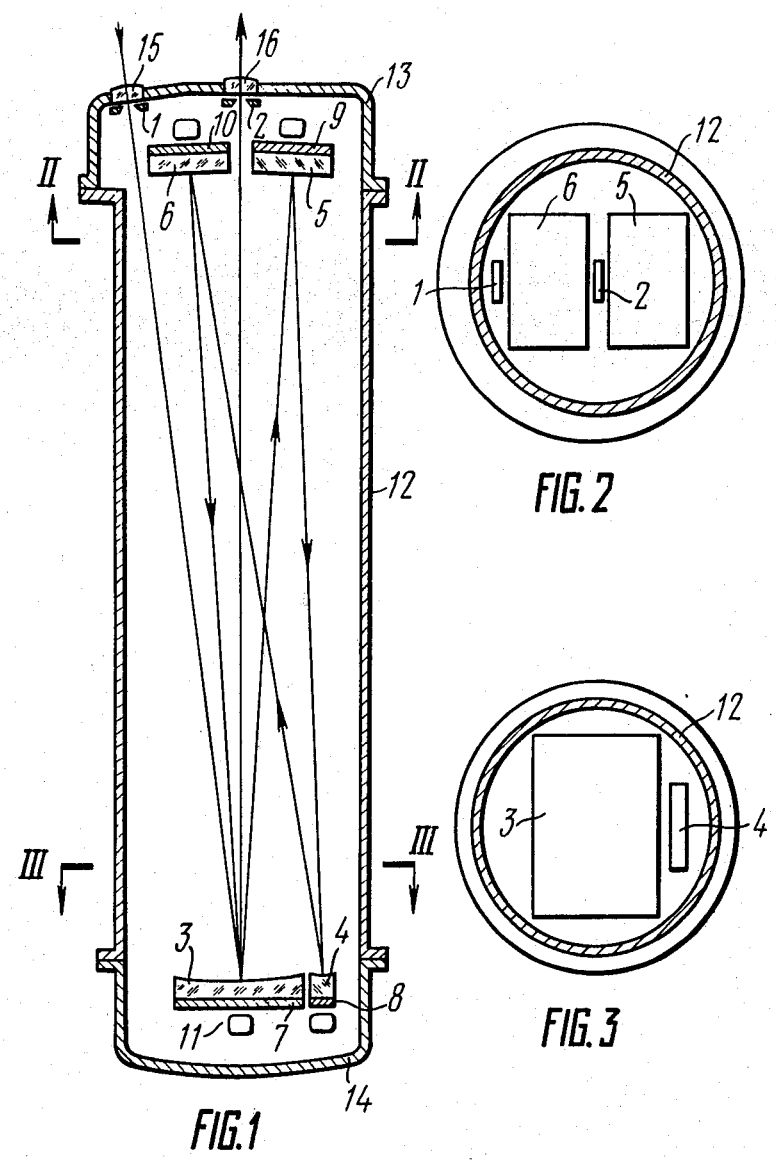
FIG. 1 is a longitudinal sectional view of a multiple reflection cell embodying the invention.
FIG. 2 is a sectional view taken on line II—II of FIG. 1.
FIG. 3 is a sectional view taken on line III—III of FIG. 1.

The optical system of multiple reflection in accordance with the invention will be further described in connection with its embodiment in a multiple reflection cell.

The multiple reflection cell comprises opposing reflecting members or units of which one is adjoined by the entrance slit 1 (FIG. 1), and the other is made up of two concave mirrors 3 and 4, the concave mirrors 3 and 4 having different geometric dimensions. Thus, the geometric dimensions of the concave mirror 3 are substantially greater than the respective geometric dimensions of the concave mirror 4 whose focal length is about 1.5 times that of the first-mentioned, greater concave mirror 3. The concave mirrors 3, 4 are spherical in the presently described embodiment. However, they may be aspherical. The reflecting member or unit adjoined by the entrance and exit slits 1 and 2, respectively, is made up of two identical flat or planar mirrors 5 and 6 defining a group symmetrical relative to the exit slit 2. To compensate for slight astigmatism in the system, the reflecting surfaces of the generally flat mirrors 5 and 6 may be specifically shaped, e.g. cylindrically or toroidally. The geometric center of the greater concave mirror 3 and the center of the exit slit 2 belong to a single straight line which is the optical axis of the system. The spacing between the group of the identical mirrors 5, 6 and the concave mirrors 3, 4 is about 1.5 times the focal length of the greater concave mirror 3. Each one of the mirrors 3, 4, 5, 6 are secured in their respective holders 7, 8, 9, 10 and are associated with a standard-type adjustment device 11. The mirror system 3, 4, 5, 6 is mounted in a sealed housing made up by a cylindrical part 12 and two lids 13 and 14. Windows 15 and 16 are mounted in the lid 13 in front of the entrance and exit slits 1 and 2, respectively.

In the presently described embodiment, the mirrors 5 and 6 (FIG. 2) are of a generally rectangular shape and are within the diameter of the cylindrical part 12 of the housing of the system. The geometric dimensions of the entrance slit 1 and of the exit slit 2 are the same.

The concave mirrors 3, 4 (FIG. 3) are likewise of a generally rectangular shape and are accommodated in the housing of the system in an optimized manner, viz. the greater concave mirror 3 is inscribed within the circle of the cylindrical part 12 of the housing, whereas the smaller mirror 4 is accommodated in the remaining unoccupied space.

The multiple reflection cell operates, as follows.

Beams from a vertically elongated light source (not shown) pass through the window 15 (FIG. 1) and the entrance slit 1 toward the concave mirror 3 which reflects them onto the flat mirror 5 which, in its turn, rotates the beams toward the other concave mirror 4, with the greater concave mirror 3 forming a magnified image of the entrance slit 1 on the surface of the smaller concave mirror 4. Further on, the smaller concave mirror 4 directs the beams onto the flat mirror 6 which, in its turn, rotates them toward the greater concave mirror 3 which reflects them for the last time and focuses them in the plane of the exit slit 2, the size being the original one. The beams thus leave the cell via the window 16.

The herein disclosed optical system being a reversible one, the beams may enter the cell via the exit slit 2 (FIG. 2) and leave it via the entrance slit 1, the principle of the operation of the cell remaining the same.

The concave mirror 4 (FIG. 3) provides for the accurate coincidence of the reflected image of the greater concave mirror 3 on itself, no beams being scattered beyond the edges of the concave mirror 3. In this way the phenomenon of inclined beam vignetting is precluded.

With the greater concave mirror 3 being inscribed within the cylindrical part 12 of the housing of the cell, the relative aperture of the system is utilized to the maximum.

The structural features of the herein described multiple reflection optical cell provided for simple and reliable adjustment of the mirrors 3, 4, 5 and 6 in separate and consequent steps. As an outcome of this, slight maladjustments of the system would not affect the stability of its performance.

As compared with the prior art, the herein disclosed multiple reflection optical system offers increased power, reduced aberration, simplified adjustments and enhanced stability of the performance of the mirrors.

What is claimed is:

1. A multiple reflection optical system comprising:
   an entrance slit adapted to pass beams therethrough;
   a first concave mirror in the path of the beams coming in through said entrance slit;
   a first mirror in the path of the beams reflected by said first concave mirror, spaced therefrom by a distance which is about 1.5 times the focal length thereof;
   a second concave mirror with a focal length which is about 1.5 times the focal length of said first concave mirror, said second concave mirror having smaller geometric dimensions than said first concave mirror, said second concave mirror being arranged in opposition to said first mirror in the path of the beam reflected thereby and spaced therefrom by a distance which is substantially equal to the focal length of said second concave mirror, said second concave mirror being arranged adjacent to said first concave mirror;
   a second mirror arranged in the same plane with said first mirror, in the path of the beams reflected by said second concave mirror;
   an exit slit arranged in the same plane with said entrance slit;
   said first and second mirrors defining a group of identical mirrors arranged symmetrically with respect to one of said slits.

* * * * *